(12) United States Patent
Chiu et al.

(10) Patent No.: US 8,647,348 B2
(45) Date of Patent: Feb. 11, 2014

(54) APPARATUS FOR ADULT CIRCUMCISION

(76) Inventors: Kwok Wai Chiu, Richardson, TX (US);
Hongtao Qiu, Dallas, TX (US)

( * ) Notice: Subject to any disclaimer, the term of this patent is extended or adjusted under 35 U.S.C. 154(b) by 2128 days.

(21) Appl. No.: 11/279,898

(22) Filed: Apr. 17, 2006

(65) Prior Publication Data

US 2007/0244516 A1 Oct. 18, 2007

(51) Int. Cl.
*A61B 17/32* (2006.01)
(52) U.S. Cl.
USPC .......................................... 606/118; 606/207
(58) Field of Classification Search
USPC .................................. 606/118, 119, 120, 207
See application file for complete search history.

(56) References Cited

U.S. PATENT DOCUMENTS

| | | | |
|---|---|---|---|
| 755,921 A * | 3/1904 | O'Neill | 606/148 |
| 2,887,111 A * | 5/1959 | Leyro Diaz | 606/148 |
| 4,605,002 A * | 8/1986 | Rebuffat | 606/148 |
| 4,648,401 A * | 3/1987 | Mattson | 606/174 |
| 4,655,223 A * | 4/1987 | Kim | 606/148 |
| 5,649,933 A | 7/1997 | Singh | |
| 5,746,748 A * | 5/1998 | Steinberg et al. | 606/118 |
| 5,860,988 A | 1/1999 | Rawlings | |
| 6,547,797 B1 * | 4/2003 | Lee | 606/118 |
| 6,780,194 B2 | 8/2004 | Freedman et al. | |

* cited by examiner

*Primary Examiner* — S. Thomas Hughes
*Assistant Examiner* — Julie A Szpira
(74) *Attorney, Agent, or Firm* — William S. Wang

(57) ABSTRACT

A circumcision clamp for aiding the removal of the foreskin of an adult, human, male penis. A top clamp and a bottom clamp for circumcision each has: 1) a curved interior brace, placed between the foreskin and the penis shaft; and 2) a curved exterior brace, which aligns over the interior brace and compresses the foreskin against the interior brace. The curved interior brace preferably has a greater depth than the exterior brace, which greater depth forms a distal overhang or shelf for protecting the penis shaft during operation. By simultaneously employing a top clamp and a bottom clamp during circumcision, an entire band or collar of foreskin along the desired path of incision and suturing can be securely held in place and clamped, thus helping the operator or surgeon trim and suture the foreskin quickly and precisely.

1 Claim, 4 Drawing Sheets

APPARATUS FOR ADULT CIRCUMCISION

BACKGROUND

1. Technical Field

The present invention relates to a circumcision clamp for use in the surgical removal of the foreskin of an adult, human, male penis. More specifically, an improved circumcision clamp enables one to easily perform a circumcision operation with ease, efficiency, and minimal bleeding.

2. Description of Related Art

Circumcision is the surgical procedure by which excess foreskin is removed from the penis. This procedure is performed throughout the world for various reasons. For some it is an ancient and mandatory ritual connected with the practice of religion; for others it is a rite of passage into manhood and full acceptance as members of their society. Furthermore, circumcisions are often performed as a result of a doctor's recommendation for medical or health reasons.

The major parts of the human penis include: the shaft or "neck" of the penis, the base of which attaches to the body in the public area; the sack-like scrotum, which suspends from the lower half of the neck; the glans penis, which forms the head of the penis at the distal end of the neck; the corona glandis, which is the round projecting border at the base of the glans; the retroglandular sulcus, which is the shallow, circumferential groove or channel behind the glans and above which the corona glandis overhangs; and the prepuce or "foreskin," which is actually a double-layer of skin shrouding the entire shaft and at least a significant portion of the glans when the penis is in a relaxed, retracted state. At the base of the penis, the skin of the shaft is continuous with that over the pubes, scrotum, and perineum. At the neck, however, it leaves the surface and becomes folded upon itself to form the prepuce, which is also termed "foreskin" or "excess foreskin."

Generally, most patients experience apprehension during a circumcision operation, particularly as adults. This is in part because a conventional circumcision typically requires a team having a surgeon and at least one assistant. Such a team typically severs the foreskin covering the glans of the penis and sutures the cut edge of the foreskin. The average operating time of a conventional circumcision operation is approximately half an hour, which can be an uncomfortably long time for the patient if he or she is conscious during the procedure.

Circumcision procedures performed using conventional instruments can often cause excessive bleeding. Many of the existing circumcision instruments cannot accommodate significant variances in the shape and size of the penis, nor do they account for the slight angle at which the glans area meets the excess foreskin.

Thus, a need exists for an improved surgical device for use in surgical procedures for removing the excess foreskin of the penis. Such a device should be simple and easy to use even by doctors having minimal training and experience in surgical procedures.

SUMMARY OF THE INVENTION

According to the present invention, a top clamp and a bottom clamp for circumcision each has: 1) a curved interior brace, which is placed at the base of the glans area between the foreskin and the penis shaft; and 2) a curved exterior brace, which aligns over the interior brace and compresses the foreskin against the interior brace. The curved interior brace (of both the top clamp and the bottom clamp) preferably has a greater depth than the exterior brace, which greater depth forms a distal overhang or shelf for protecting the penis shaft during excision of the excess foreskin. By simultaneously employing a top clamp and a bottom clamp in accordance with the present invention during a circumcision procedure, an entire band or collar of foreskin—along the desired path of incision and suturing—can be securely held in place and clamped with sufficient pressure to minimize bleeding without cutting circulation, thus helping the operator or surgeon trim and suture the foreskin quickly and precisely.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

REFERENCE NUMERALS

Figure 1:
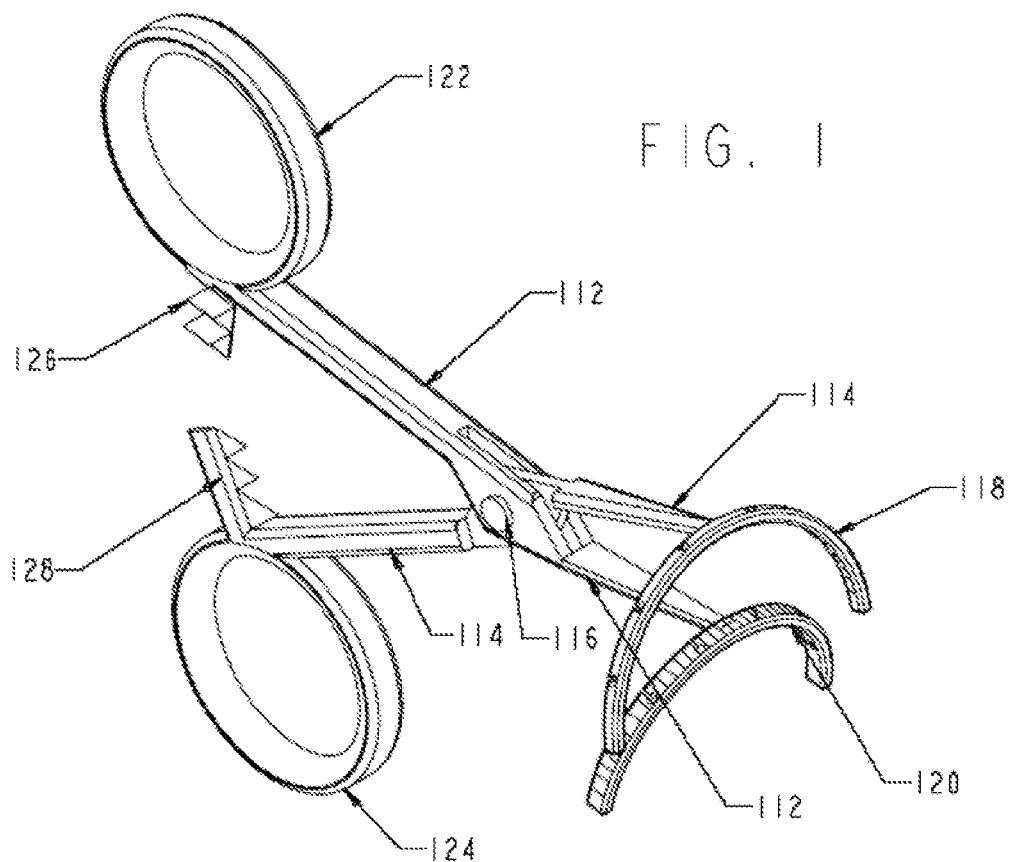
FIG. 1 is a perspective view of a top circumcision clamp for clamping and removing the upper portion of excess foreskin according to the present invention.
Figure 2:
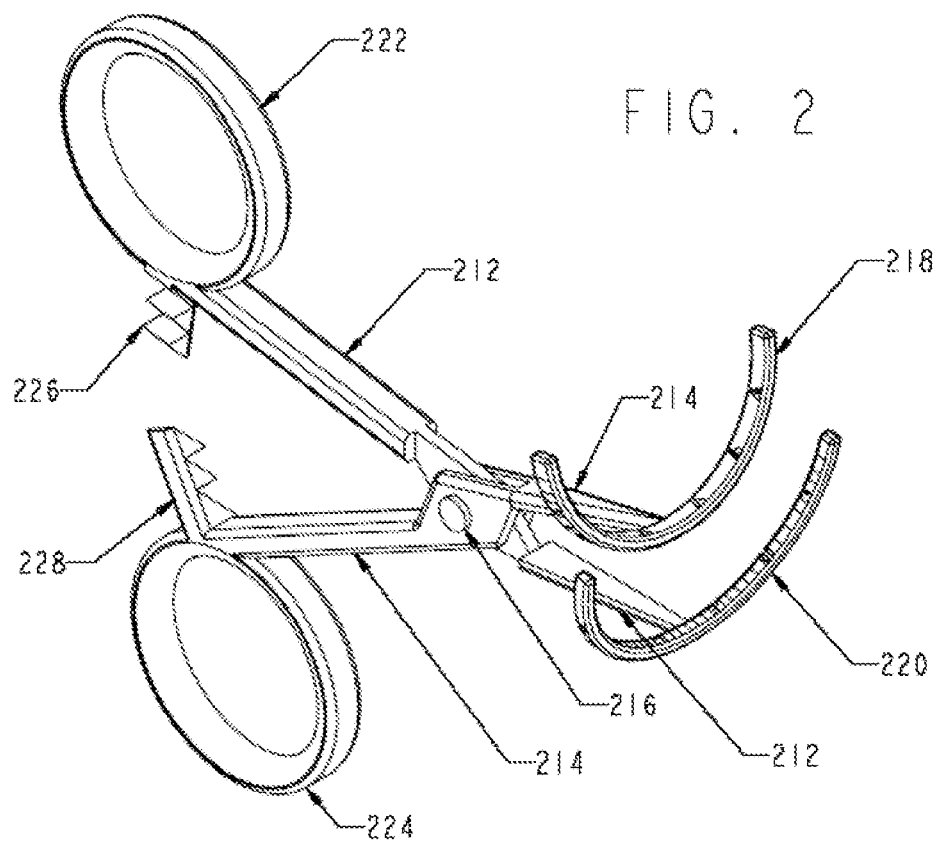
FIG. 2 is a perspective view of a bottom circumcision clamp for clamping and removing the lower portion of excess foreskin according to the present invention.

112 top-clamp interior-brace cross-member
114 top-clamp exterior-brace cross-member
116 top-clamp pivot pin
118 top-clamp exterior brace
120 top-clamp interior brace
122 top-clamp thumb loop
124 top-clamp finger loop
126 top-clamp upper locking tabs
128 top-clamp lower locking tabs
130 top-clamp tilt
132 top-clamp interior-brace surface element
134 top-clamp interior-brace suture hole(s)
136 top-clamp exterior-brace surface element
138 top-clamp exterior-brace suture hole(s)
212 bottom-clamp exterior-brace cross-member
214 bottom-clamp interior-brace cross-member
216 bottom-clamp pivot pin
218 bottom-clamp interior brace
220 bottom-clamp exterior brace
222 bottom-clamp thumb loop
224 bottom-clamp finger loop
226 bottom-clamp upper locking tabs
228 bottom-clamp lower locking tabs 230 bottom-clamp tilt
232 bottom-clamp exterior-brace surface element
234 bottom-clamp exterior-brace suture hole(s)
236 bottom-clamp interior-brace surface element
238 bottom-clamp interior-brace suture hole(s)

DETAILED DESCRIPTION

While the invention is described below with respect to a preferred embodiment other embodiments are possible. The concepts disclosed herein apply equally to other circumcision clamps of other shapes and designs, provided that they follow the spirit of the teachings disclosed herein.

Whereas many prior art circumcision devices simply cut excess foreskin along a plane generally perpendicular to the penis at issue, the present invention enables one to remove the excess foreskin at a slight angle corresponding to the angled-interface at which the base of the excess foreskin meets the base of the glans area of the penis. Such contoured excision of the excess foreskin is made possible with two separate semi-circular clamps—a top clamp and a bottom clamp—as disclosed herein.

According to the present invention, the top clamp and the bottom clamp each has: 1) a curved interior brace, which is placed at the base of the glans area between the foreskin and the penis shaft; and 2) a curved exterior brace, which aligns over the interior brace and compresses fore foreskin against the interior brace. More specifically, the interior brace of the top clamp is placed just above the top half of the glans at the glans base but within the foreskin tube, while the exterior brace of the top clamp aligns above the interior brace so it can clamp down upon the upper half of the foreskin. Similarly, the interior brace of the bottom clamp is placed just below the bottom half of the glans at the glans base but within the foreskin tube, while the exterior brace of the bottom clamp aligns below the interior brace so it can clamp up upon the lower half of the foreskin. The curved interior brace (of both the top clamp and the bottom clamp) preferably has a greater depth than the exterior brace, which greater depth forms a distal overhang or shelf for protecting the penis shaft during excision of the excess foreskin. By simultaneously employing a top clamp and a bottom clamp in accordance with the present invention during a circumcision procedure, an entire band or collar of foreskin—along the desired path of incision and suturing—can be securely held in place and clamped with sufficient pressure to minimize bleeding without cutting circulation, thus helping the operator or surgeon trim and suture the foreskin quickly and precisely.

In a preferred embodiment, and with reference to FIGS. 1, 3, 5, and 7, a top clamp includes the following elements, the connectivity and operation of which will be further described below: a top-clamp ("TC") interior-brace cross-member 112; a TC exterior-brace cross-member 114; a TC pivot pin 116 pivotally connecting the TC interior-brace cross-member 112 and the TC exterior-brace cross-member 114 together at their general midsections, thereby enabling the TC exterior-brace cross-member 114 and the TC interior-brace cross-member 112 to pivot freely about the TC pivot pin 116; a TC exterior brace 118 at the distal end (relative to the user) of the TC exterior-brace cross-member 114; a TC interior brace 120 at the distal end of the TC interior-brace cross-member 112; a TC thumb loop 122 at the proximal end of the TC interior-brace cross-member 112; a TC finger loop 124 at the proximal end of the TC exterior-brace cross-member 114; a plurality of TC upper locking tabs 126 at the proximal end of the TC interior-brace cross-member 112 and extending towards the TC exterior-brace cross-member 114; a plurality of TC lower locking tabs 128 at the proximal end of the TC exterior-brace cross-member 114 and extending towards the TC interior-brace cross-member 112; a TC tilt angle 130, which is slightly acute; a TC interior-brace surface element 132; a plurality of TC interior-brace suture holes 134; a TC exterior-brace surface element 136; and a plurality of TC exterior-brace suture holes 138.

For the construction of the top clamp and the bottom clamp, suitable materials include: any medical-grade metal or alloy, such as stainless steel, any medical-grade plastic, any medical-grade composite, any medical-grade ceramic, such as aluminum oxide, zirconium oxide, silicon nitride aluminum nitride, and silicon carbide, as long as the material chosen is (or materials chosen are) sufficiently rigid to apply the clamping pressure needed to secure the double-layer prepuce for operation and minimize bleeding without completely blocking circulation to the clamped tissue.

In a preferred embodiment, the TC exterior brace 118 and the TC interior brace 120 are semicircular, complementary, and concentric, such that when the top clamp is in a closed, clamping position, the lower surface of the TC exterior brace 118 mates with (or, at a minimum, fits closely over although not necessarily contacting) the upper surface of the TC interior brace 120. The general diameter of the TC interior brace 120 and TC exterior brace 118 can range from roughly 1 centimeter to several centimeters, corresponding to the typical range of penile shaft/neck diameters. The diameter of the TC interior brace 120, of course, will be slightly less than that of the TC exterior brace 118 so that the two can properly mate and therebetween clasp the patient's foreskin. The TC interior brace 120 depth is prefer ably slightly greater than the TC exterior brace 118 depth, such that the TC interior brace 120 protrudes in the proximal direction slightly beyond the proximal edge of the TC exterior brace 118. This protruding section of the TC interior brace 120 forms a base or shelf upon which the operator/surgeon can cut the foreskin without fear of undesirably piercing the neck/shaft portion of the penis; thus, the protruding shelf of the TC interior brace 120 helps prevent accidental piercing during operation. Note that the material selected for the TC interior brace 120 should be of sufficient hardness to withstand, for at least one operation, being cut upon without dismemberment of the shelf portion from the remainder of the TC interior brace 120. In a disposable embodiment of the present invention, the TC interior brace 120 would need sufficient hardness to withstand merely one use, whereas a reusable embodiment would require greater hardness. Thus, a disposable embodiment can be made from medical-grade hard plastic, while a reusable embodiment will require a more durable, harder substance such as medical-grade ceramic, metal, or metal alloy.

The TC interior brace 120 has a plurality of TC interior-brace suture holes 134 through which suturing threads or stitches can be run. Likewise, the TC exterior brace 118 has a plurality of TC exterior-brace suture holes 138 through which suturing threads or stitches can be run. Preferably, each one of the plurality of TC exterior-brace suture holes 138 and the plurality of TC interior-brace suture holes 134 has a key-shaped profile generally comprising: a round needle hole sufficiently large enough to accommodate a suturing needle, and a narrow channel or slit leading from the distal edge of the bracing element to the needle hole. The plurality of TC exterior-brace suture holes 138 and the plurality of TC interior-brace suture holes 134 enable the operator/surgeon to suture the remaining, freshly-cut portion of the foreskin without removing the clamp. Without having to remove the clamp during suturing, the operator/surgeon is able to keep the clamped area of the foreskin taught and in place for suturing, as well as minimize bleeding.

The TC interior-brace surface element 132 and the TC exterior-brace surface element 136 add texture, increase surface area, and increase the coefficient of friction on the otherwise-smooth gripping-and-clamping surfaces of the TC interior brace 120 and the TC exterior brace 118. The TC interior-brace surface element 132 and the TC exterior-brace surface element 136 can be embossed or raised patterns, such as parallel lines or hatched lines. Alternatively, such elements can be complementary, corrugated surfacing, or they can be complementary teeth, or even surface cuts or etching. In yet another embodiment, the TC interior-brace surface element 132 and the TC exterior-brace surface element 136 are simply raised dots or bumps. Such elements are well-known in the art and need not be described in further detail.

The plurality of TC upper locking tabs 126 and the plurality of TC lower locking tabs 128 can comprise interlocking facets, which facets are capable of slight lateral displacement while under pressure from abutment against adjacent facets, thereby enabling the interlocking of adjacent facets and enabling the TC interior-brace cross-member 112, the TC exterior-brace cross-member 114, the TC interior brace 120, and the TC exterior brace 118 to be fixed in one or more clamping positions. Such locking tabs are well-known in the art and need not be described in further detail.

Figure 3:
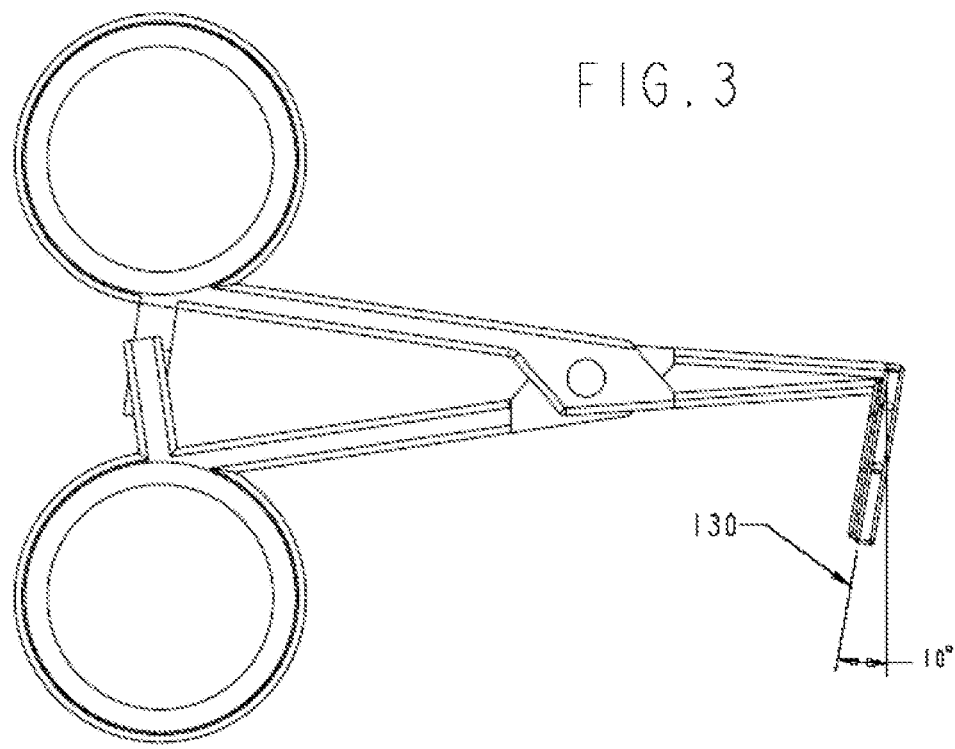
FIG. 3 is a side, elevated view of the top circumcision clamp of FIG. 1 showing the slightly-acute angle of the bracing elements relative to the longitudinal axis of the clamp.

Note that the clamping portion of the top clamp has a TC tilt angle 130 (or "clamp-brace tilt angle"), as is most evident in FIG. 3. More specifically, the TC interior brace 120 and the TC exterior brace 118 align together within a plane that forms an acute angle with the shared, longitudinal axis of the TC interior-brace-cross-member 112 and the TC exterior-brace cross-member 114. In a preferred embodiment, this TC tilt 130 is on the order of a few degrees, and most preferably about 10° (degrees) in the acute direction from the right-angle position (perpendicular, 90°). The TC tilt 130 corresponds with the slightly-angled, non-perpendicular retroglandular sulcus and corona glandis.

In a preferred embodiment, and with respect to FIGS. 2, 4, 6, and 8, a bottom clamp includes the following elements, the connectivity and operation of which will be further described below: a bottom-clamp ("BC") exterior-brace cross-member 212; a BC interior-brace cross-member 214; a BC pivot pin 216 pivotally connecting the BC exterior-brace cross-member 212 and the 214 together at their general midsections, thereby enabling the BC interior-brace cross-member 214 and the BC exterior-brace cross-member 212 to pivot freely about the BC pivot pin 216; a BC interior brace 218 at the distal end (relative to the user) of the BC interior-brace cross-member 214; a BC exterior brace 220 at the distal end of the BC exterior-brace cross-member 212; a BC thumb loop 222 at the proximal end of the BC exterior-brace cross-member 212; a BC finger loop 224 at the proximal end of the BC interior-brace cross-member 214; a plurality of BC upper locking tabs 226 at the proximal end of the BC thumb loop 222 and extending towards the BC interior-brace cross-member 214; a plurality of BC lower locking tabs 228 at the proximal end of the BC interior-brace cross-member 214 and extending towards the BC exterior-brace cross-member 212; a BC tilt angle 230, which is slightly obtuse; a BC exterior-brace surface element 232; a plurality of BC exterior-brace suture hole(s) 234; a BC interior-brace surface element 236; and a plurality of BC interior-brace suture hole(s) 238.

In a preferred embodiment, the BC interior brace 218 and the BC exterior brace 220 are semicircular, complementary, and concentric, such that when the bottom clamp is in a closed, clamping position, the lower surface of the BC interior brace 218 mates with (or, at a minimum, fits closely over although not necessarily contacting) the upper surface of the BC exterior brace 220. The general diameter of the BC interior brace 218 and the BC exterior brace 220 can range from roughly 1 centimeter to several centimeters, corresponding to the typical range of penile shaft/neck diameters. The diameter of the BC interior brace 218, of course, will be slightly less than that of the BC exterior brace 220 so that the two can properly mate and therebetween clasp the patient's foreskin. The BC interior brace 218 depth is preferably slightly greater than the BC exterior brace 220 depth, such that the BC interior brace 218 protrudes in the proximal direction slightly beyond the proximal edge of the BC exterior brace 220. This protruding section of the BC interior brace 218 forms a base or shelf upon which the operator/surgeon can cut the foreskin without fear of undesirably piercing the neck/shaft portion of the penis; thus, the protruding shelf of the BC interior brace 218 helps prevent accidental piercing during operation. Note that the material selected for the BC interior brace 218 should be of sufficient hardness to withstand, for at least one operation, being cut upon without dismemberment of the shelf portion from the remainder of the BC interior brace 218. In a disposable embodiment of the present invention, the BC interior brace 218 would need sufficient hardness to withstand merely one use, whereas a reusable embodiment would require greater hardness. Thus, a disposable embodiment can be made from medical-grade hard plastic, while a reusable embodiment will require a more durable, harder substance such as medical-grade ceramic, metal, or metal alloy.

The BC interior brace 218 has a plurality of BC interior-brace suture hole(s) 238 through which suturing threads or stitches can be run. Likewise, the BC exterior brace 220 has a plurality of BC exterior-brace suture hole(s) 234 through which suturing threads or stitches can be run. Preferably, each one of the plurality of BC interior-brace suture hole(s) 238 and the plurality of BC exterior-brace suture hole(s) 234 has a key-shaped profile generally comprising a round needle hole sufficiently large enough to accommodate a suturing needle; and a narrow channel or slit leading from the distal edge of the bracing element to the needle hole. The plurality of BC interior-brace suture hole(s) 238 and the plurality of BC exterior-brace suture hole(s) 234 enable the operator/surgeon to suture the remaining, freshly-cut portion of the foreskin without removing the clamp. Without having to remove the clamp during suturing, the operator/surgeon is able to keep the clamped area of the foreskin taught and in place for suturing, as well as minimize bleeding.

The BC interior-brace surface element 236 and the BC exterior-brace surface element 232 add texture, increase surface area, and increase the coefficient of friction on the otherwise-smooth gripping-and-clamping surfaces of the BC interior brace 218 and the BC exterior brace 220. The BC interior-brace surface element 236 and the BC exterior-brace surface element 232 can be embossed or raised patterns, such as parallel lines or hatched lines. Alternatively, such elements can be complementary, corrugated surfacing, or they can be complementary teeth, or even surface cuts or etching. In yet another embodiment, the BC interior-brace surface element 236 and the BC exterior-brace surface element 232 are simply raised dots or bumps. Such elements are well-known in the art and need not be described in further detail.

The plurality of BC upper locking tabs 226 and the plurality of BC lower locking tabs 228 can comprise interlocking facets, which facets are capable of slight lateral displacement while under pressure from abutment against adjacent facets, thereby enabling the interlocking of adjacent facets and enabling the BC interior-brace cross-member 214, the BC exterior-brace cross-member 212, the BC interior brace 218, and the BC exterior brace 220 to be fixed in one or more clamping positions. Such locking tabs are well-known in the art and need not be described in further detail.

Figure 4:
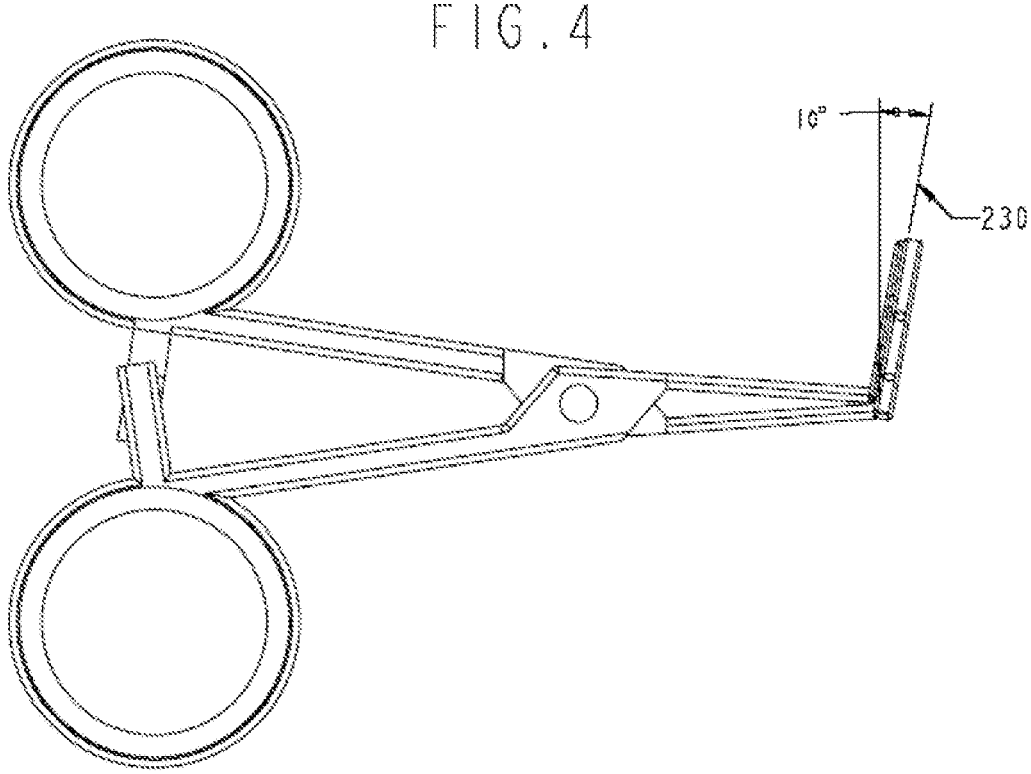
FIG. 4 is a side, elevated view of the bottom circumcision clamp of FIG. 2 showing the slightly-obtuse angle of the bracing elements relative to the longitudinal axis of the clamp.
Figure 5:
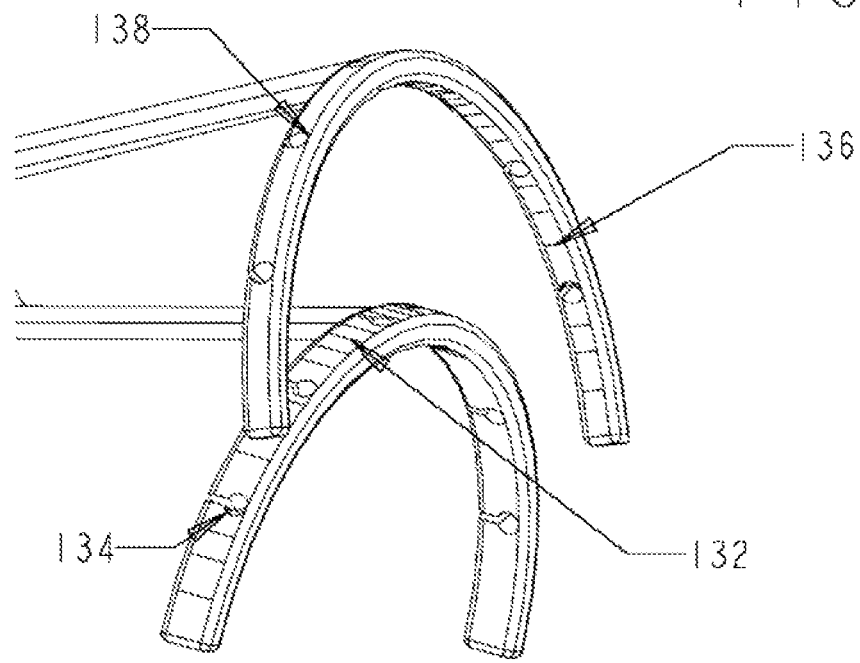
FIG. 5 is a partial, enlarged perspective view of the interior brace and exterior brace of the top circumcision clamp of FIG. 1.
Figure 6:
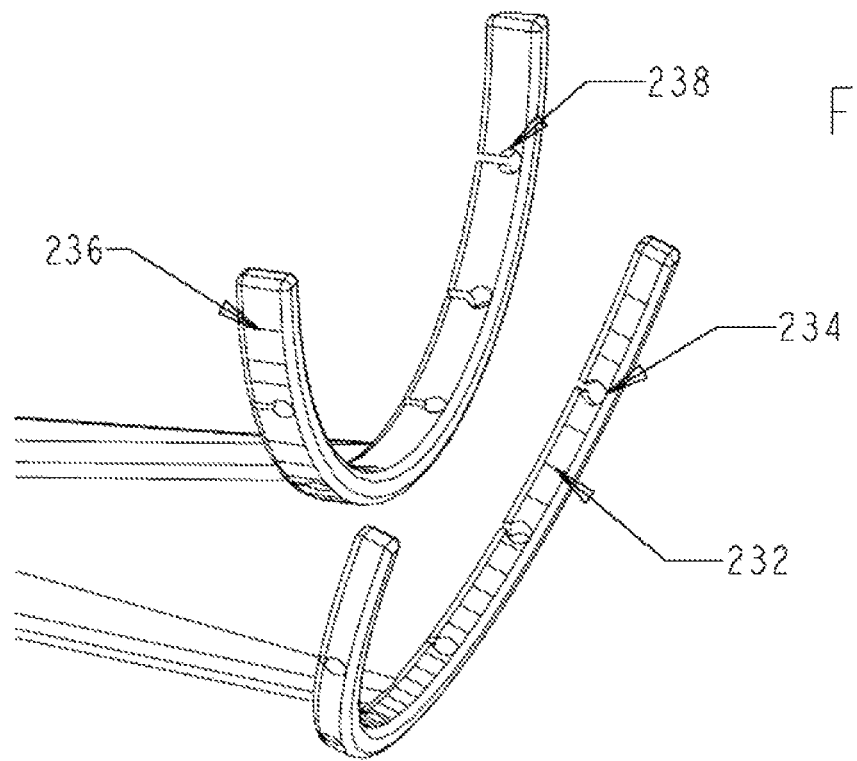
FIG. 6 is a partial, enlarged, perspective view of the interior brace and exterior brace of the bottom circumcision clamp of FIG. 2.
Figure 7:
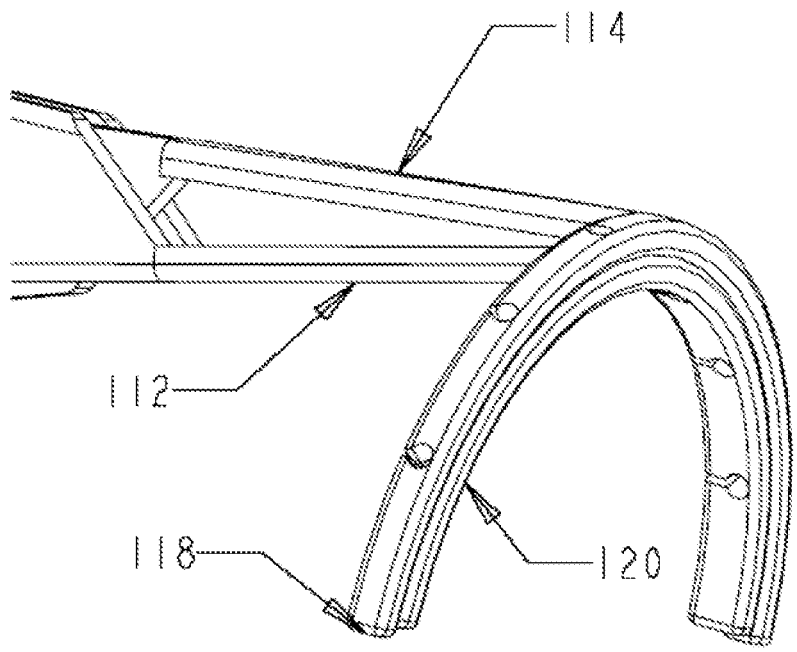
FIG. 7 is a partial, enlarged, perspective view of the top clamp of FIG. 1, closed.
Figure 8:
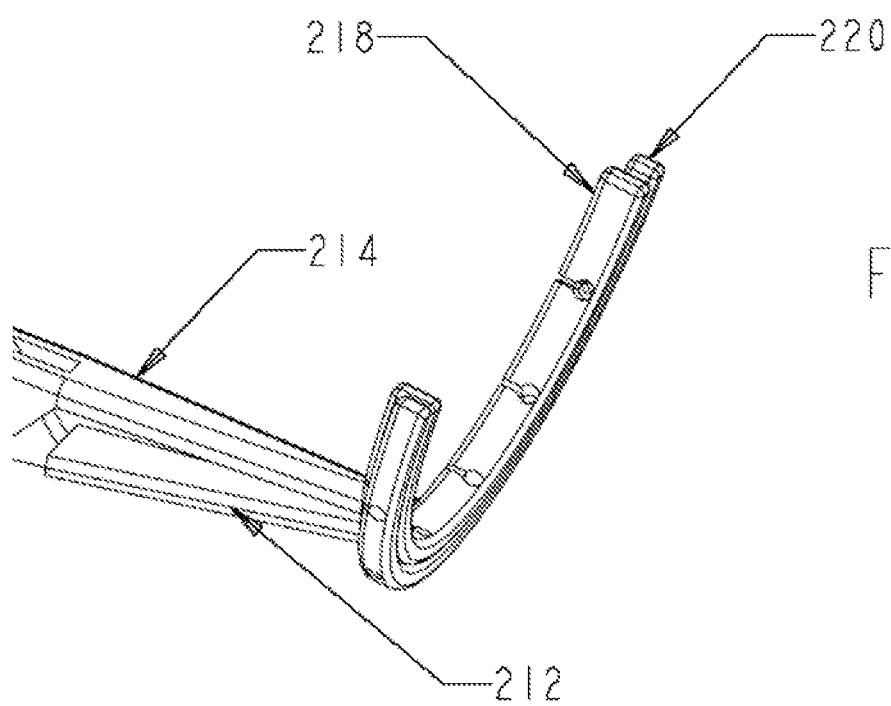
FIG. 8 is a partial, enlarged, perspective view of the bottom clamp of FIG. 2, closed.

Note that the clamping portion of the bottom clamp has a BC tilt angle 230 (or "clamp-brace tilt angle"), as is most evident in FIG. 4. More specifically, the BC interior brace 218 and the BC exterior brace 220 align together within a plane that forms an obtuse angle with the shared longitudinal axis of the BC interior-brace cross-member 214 and the BC exterior-brace cross-member 212. In a preferred embodiment, this BC tilt 230 is on the order of a few degrees, and most preferably about 10° (degrees) in the obtuse direction beyond the night-angle position. The BC tilt 230 corresponds with the slightly-angled, non-perpendicular retroglandular sulcus and corona glandis.

While the invention has been particularly shown and described with reference to a preferred embodiment, it will be understood by those skilled in the art that various changes in form and detail may be made therein without departing from the spirit and scope of the invention.

We claim:

1. A circumcision clamp for assisting in the removal of the foreskin of the penis of an adult human male, said circumcision clamp comprising:
    an interior-brace cross-member;
    an exterior-brace cross-member;
    a pivot pin pivotally connecting the interior-brace cross-member and the exterior-brace cross-member together at their general midsections, thereby enabling the exterior-brace cross-member and the interior-brace cross-member to pivot freely about the pivot pin;
    an exterior brace at the distal end of the exterior-brace cross-member, wherein said exterior brace is curved;
    an interior brace at the distal end of the interior-brace cross-member, wherein said interior brace is curved;
    a first loop at the proximal end of the interior-brace cross-member;
    a second loop at the proximal end of the exterior-brace cross-member;
    a plurality of first-loop locking tabs at the proximal end of the interior-brace cross-member and extending towards the exterior-brace cross-member;
    a plurality of second-loop locking tabs at the proximal end of the exterior-brace cross-member and extending towards the interior-brace cross-member;
    a clamp-brace tilt angle;
    an interior-brace surface element;
    a plurality of interior-brace suture holes;
    an exterior-brace surface element; and
    a plurality of exterior-brace suture holes;
  wherein:
    said exterior brace and said interior brace are semicircular and complementary such that when the circumcision clamp is in a closed position, the interior brace has a smaller diameter than, and is concentric within, said exterior brace;
    said clamp-brace tilt angle is on the order of a few degrees and refers to an acute angle formed between the length of the circumcision clamp, in a closed position, and the axis of curvature shared by the interior brace and the exterior brace; and
    said interior brace has a depth greater than that of the exterior brace, such that the interior brace protrudes in the proximal direction beyond the proximal edge of the exterior brace.

* * * * *